US008433398B2

(12) United States Patent
Zhang

(10) Patent No.: US 8,433,398 B2
(45) Date of Patent: Apr. 30, 2013

(54) SIGNAL ANALYSIS SYSTEM FOR HEART CONDITION DETERMINATION

(75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 13/314,227

(22) Filed: Dec. 8, 2011

(65) Prior Publication Data
US 2012/0232417 A1 Sep. 13, 2012

Related U.S. Application Data

(60) Provisional application No. 61/451,182, filed on Mar. 10, 2011.

(51) Int. Cl.
A61B 5/02 (2006.01)
(52) U.S. Cl.
USPC ........... 600/518; 600/512; 600/513; 600/515; 600/516; 600/517
(58) Field of Classification Search .................. None
See application file for complete search history.

(56) References Cited

U.S. PATENT DOCUMENTS

| | | |
|---|---|---|
| 5,188,177 A | 2/1993 | Curry |
| 5,486,199 A | 1/1996 | Kim et al. |
| 5,522,852 A | 6/1996 | White et al. |
| 5,542,430 A | 8/1996 | Farrugia et al. |
| 5,549,641 A | 8/1996 | Ayers et al. |
| 5,683,429 A | 11/1997 | Mehra |
| 5,788,717 A | 8/1998 | Mann et al. |
| 5,817,134 A | 10/1998 | Greenhut et al. |
| 5,843,133 A | 12/1998 | Routh et al. |
| 5,853,426 A | 12/1998 | Shieh |
| 5,968,079 A | 10/1999 | Warman et al. |
| 5,983,162 A | 11/1999 | Huang |
| 6,041,251 A | 3/2000 | Kim et al. |
| 6,064,906 A | 5/2000 | Langberg et al. |
| 6,178,347 B1 | 1/2001 | Olsson |
| 6,263,244 B1 | 7/2001 | Mann et al. |
| 6,285,908 B1 | 9/2001 | Mann et al. |
| 6,408,205 B1 | 6/2002 | Renirie et al. |
| 6,490,479 B2 | 12/2002 | Bock |
| 6,597,943 B2 | 7/2003 | Taha et al. |
| 6,618,622 B1 | 9/2003 | Mann et al. |
| RE38,515 E | 5/2004 | White |

(Continued)

OTHER PUBLICATIONS

Joao Tranchesi M.D.; Victor Adelardi M.D.; Jorge Martins De Oliveira M.D., "Atrial Repolarization—Its Importance in Clinical Electrocardiography", Circulation, 1960; vol. 22, p. 635-644.

(Continued)

Primary Examiner — Brian T Gedeon
Assistant Examiner — Ankit Tejani
(74) Attorney, Agent, or Firm — Alexander J Burke

(57) ABSTRACT

A system for heart performance characterization and abnormality detection includes an interface for receiving sampled data representing an electrical signal indicating electrical activity of a patient heart over multiple heart beat cycles. A signal processor automatically, decomposes the received sampled data to multiple different subcomponent signals in the time domain. The signal processor associates individual decomposed subcomponents with corresponding different cardiac rotors and determined characteristics of the subcomponents indicating relative significance of the rotors in a cardiac atrial condition. A reproduction device provides data indicating the subcomponent characteristics indicating relative significance of the rotors in a cardiac atrial condition.

23 Claims, 13 Drawing Sheets

U.S. PATENT DOCUMENTS

| | | | |
|---|---|---|---|
| 6,738,655 | B1 | 5/2004 | Sen et al. |
| 6,738,664 | B1 | 5/2004 | McDaniel |
| 6,937,887 | B2 | 8/2005 | Bock |
| 6,968,226 | B2 | 11/2005 | Mehra et al. |
| 7,092,751 | B2 | 8/2006 | Erkkila |
| 7,117,029 | B2 | 10/2006 | Stridh et al. |
| 7,123,954 | B2 | 10/2006 | Narayan et al. |
| 7,142,912 | B2 | 11/2006 | Wagner et al. |
| 7,153,301 | B2 | 12/2006 | Swartz et al. |
| 7,177,682 | B2 | 2/2007 | Lovett |
| 7,321,794 | B2 | 1/2008 | Thacker et al. |
| 7,328,066 | B1 | 2/2008 | Levine |
| 7,519,421 | B2 | 4/2009 | Denker et al. |
| 7,627,368 | B2 | 12/2009 | Houben et al. |
| 7,634,310 | B2 | 12/2009 | Lee et al. |
| 7,643,878 | B1 | 1/2010 | Muller et al. |
| 7,783,352 | B1 | 8/2010 | Ryu et al. |
| 2005/0038480 | A1* | 2/2005 | Ding .................................. 607/9 |
| 2008/0097537 | A1* | 4/2008 | Duann et al. .................... 607/14 |
| 2009/0281441 | A1* | 11/2009 | Zhang et al. .................. 600/516 |
| 2009/0292180 | A1* | 11/2009 | Mirow .......................... 600/301 |

OTHER PUBLICATIONS

F Jousset1, JM Vesin1, P Pascale2, P Ruchat2, S C Schaefer2, M Fromer2, E Pruvot, "In Vivo Measurements of Atrial Repolarization Alternans Based on Standard Pacemaker Technology", Computers in Cardiology, 2009; vol. 36, p. 145-148.

P Langley, M Stridh, JJ Rieta, L Sörnmo, J Millet-Roig, A Murray, "Comparison of Atrial Rhythm Extraction Techniques for the Estimation of the Main Atrial Frequency from the 12-lead Electrocardiogram in Atrial Fibrillation", Computers in Cardiology, 2002, vol. 29, p. 29-32.

Gang Wang, Ni-ni Rao, Simon J. Shepherd, and Clive B. Beggs, "Extraction of Desired Signal Based on AR Model with Its Application to Atrial Activity Estimation in Atrial Fibrillation", EURASIP Journal on Advances in Signal Processing, vol. 2008, Article ID 728409,9 Pages.

Martin Stridh, Andreas Bollmann, S.Bertil Olsson, and Leif Sörnmo, "Detection and Feature Extraction of Atrial Tachyarrhythmias, A three stage method of time-frequency analysis", IEEE Engineering in Medicine and Biology Magazine, Nov.-Dec. 2006, vol. 25, No. 6, p. 31-9.

José Joaquín Rieta, Francisco Castells, César Sánchez, Vicente Zarzoso, and José Millet, "Atrial Activity Extraction for Atrial Fibrillation Analysis Using Blind Source Separation", IEEE Transactions on Biomedical Engineering, Vol. 51, No. 7, Jul. 2004, p. 1176-1186.

Dan Rainse, Philip Langley, etc, "Surface atrial frequency analysis in patients with atrial fibrillation: a tool for evaluating the effects of intervention", Journal of cardiovascular electrophysiology, vol. 15, No. 9, Sep. 2004, p. 1021-1026.

Francisco Castells, Pablo Laguna, Leif S ornmo, Andreas Bollmann, and Jos'eMillet Roig, "Principal Component Analysis in ECG Signal Processing", EURASIP Journal on Advances in Signal Processing, vol. 2007, issue 1, 2007, 21 pages.

Leif Sornmo, Martin Stridh, Daniela Husser,Andreas Bollmann, and S. Bertil Olsson, "Analysis of atrial fibrillation: from electrocardiogram signal processing to clinical management", Phil. Trans. R. Soc. A (2009) 367, 235-253.

\* cited by examiner

Figure 6

| Signal names | | Signal function and definition |
|---|---|---|
| Atrial electrophysiological signals and activities | $C_1$ | Fast rotor component 1 |
| | $C_2$ | Fast rotor component 2 |
| | $C_3$ | Middle rotor component 1 |
| | $C_4$ | Middle rotor component 2 |
| | $C_5$ | slow rotor component 1 |
| | ... | ... |

605
607

> US 8,433,398 B2

SIGNAL ANALYSIS SYSTEM FOR HEART CONDITION DETERMINATION

This is a non-provisional application of provisional application Ser. No. 61/451,182 filed Mar. 10, 2011, by H. Zhang.

FIELD OF THE INVENTION

This invention concerns a system for heart performance characterization and abnormality detection by decomposing a heart activity electrical signal to multiple different subcomponent signals in the time domain associated with corresponding different cardiac rotors.

BACKGROUND OF THE INVENTION

Atrial arrhythmia, especially Atrial Fibrillation (AF), is a common cardiac arrhythmia which may contribute to significant risk of electrophysiological disorders, leading to morbidity thrombo-embolism and stroke. Different atrial excitation rotors and their activities are factors causing complex pattern and irregular rhythm in an atrium. Atrial arrhythmia, such as AF, is a common cardiac pathology in the senior population, and is an arrhythmia, an irregularity of the heart's rhythm. Atrial fibrillation is the most prevalent tachyarrhythmia and continues to gain increasing prevalence with the aging of the population, reaching 2.3% after 40 yr of age and 10% after 80 yr of age. Recent studies indicate that AF is a common abnormal cardiac rhythm but the treatment of AF is difficult because there is no precise qualitative and quantitative methodology to analyze AF and the response to the therapy is unpredictable. Instead of only one area in the atrium starting an electrical signal, many areas send out electrical signals. The electrical impulses or wavelets spread over the atrial tissue and cause the atrial muscle to quiver or fibrillate, instead of to contract in an organized way. Some of the electrical impulses travel down through the heart and make the bottom chambers squeeze or contract. The irregularity of the impulses traveling down from the atria makes the ventricles beat irregularly, so if you take your pulse it may feel irregular. Sometimes AF can make the pulse fast and irregular or slow and irregular.

A heart in atrial fibrillation doesn't beat efficiently. It may not be able to pump enough blood out to a body with each heartbeat. Due to insufficient blood supply to the body, the heart may drastically increase the heart beat. For example the heart rate in atrial fibrillation may range from 100 to 175 beats per minute. The normal range for a heart rate is 60 to 100 beats per minute. AF alone is not a life-threatening arrhythmia, but it can be extremely bothersome and sometimes dangerous. For example, in atrial fibrillation, a chaotic rhythm may cause blood to pool in an atria and form clots. If a blood clot forms, it could dislodge from a heart and travel to the brain. There it might block blood flow, causing a stroke. The risk of stroke in atrial fibrillation depends on age (risk increases with age) and on whether a patient has high blood pressure, diabetes, or a history of heart failure or previous stroke, and other factors. Atrial fibrillation can be paroxysmal (episodes come and go on their on), persistent (episodes come and last until a heart is put back into rhythm) or permanent (the heart stays in AF despite efforts to convert into a normal rhythm). There are many causes and factors which may induce a heart into atrial fibrillation, such as high blood pressure, atrial or valve abnormality, alcohol, family history.

Early detection and treatment is desirable to reduce risk and terminate discomfort and bring the heart back to normal heart rhythm perhaps by using proper energy based cardioverter shock treatment. Early cardiac atrial arrhythmia and pathology recognition is desirable for rhythm management of cardiac disorders and irregularities. Known system analysis of atrial arrhythmia focus on P wave analysis associated with a depolarization procedure of the atrium. In a number of cases, overall P wave morphology and signal changes (atrial depolarization signals) alone may not be able to provide enough reliable arrhythmia information for early detection and characterization of atrial pathologies and malfunctions.

Known methods for complex cardiac atrial arrhythmia identification using a surface ECG signal are subjective and need extensive expertise for accurate interpretation and appropriate cardiac rhythm management, especially in an early stage of atrial fibrillation in which P wave morphology and signal changes are small and atrial arrhythmias are not easy to detect. It is known that many atrial arrhythmias are due to multi-rotor based excitations in the atrial chamber, which lead to complex patterns in atrial electrophysiology and activities. However known systems lack qualitative and quantitative methods for detection and characterization of abnormal atrial rotors. Known systems perform atrial arrhythmia (such as fibrillation) analysis and provide methods for detecting and treating atrial pathology, such as heart rate variability using medication and implantable cardioverters. However known systems may fail to detect atrial arrhythmia, especially in a noisy environment since atrial activity may be buried in noise and artifacts. Known atrial arrhythmia analysis in the time domain (e.g. of signal amplitude) and frequency domain (signal FFT) are used for monitoring but typically require interpretation by a physician with extensive experience. A system according to invention principles addresses these deficiencies and related problems.

SUMMARY OF THE INVENTION

A system improves detection of cardiac atrial electrophysiological activities, by analyzing atrial electrophysiological signals (including surface ECG signals and intra-cardiac electrograms) in response to fast and slow atrial rotor activity data extraction within a P wave signal portion, for example. A system for heart performance characterization and abnormality detection includes an interface for receiving sampled data representing an electrical signal indicating electrical activity of a patient heart over multiple heart beat cycles. A signal processor automatically decomposes the received sampled data to multiple different subcomponent signals in the time domain. The signal processor associates individual decomposed subcomponents with corresponding different cardiac rotors and determined characteristics of the subcomponents indicating relative significance of the rotors in a cardiac atrial condition. A reproduction device provides data indicating the subcomponent characteristics indicating relative significance of the rotors in a cardiac atrial condition.

BRIEF DESCRIPTION OF THE DRAWING

FIG. 6 shows a table of sub-level component signals of an atrial electrophysiological signal, according to invention principles.

DETAILED DESCRIPTION OF THE INVENTION

Figure 1:
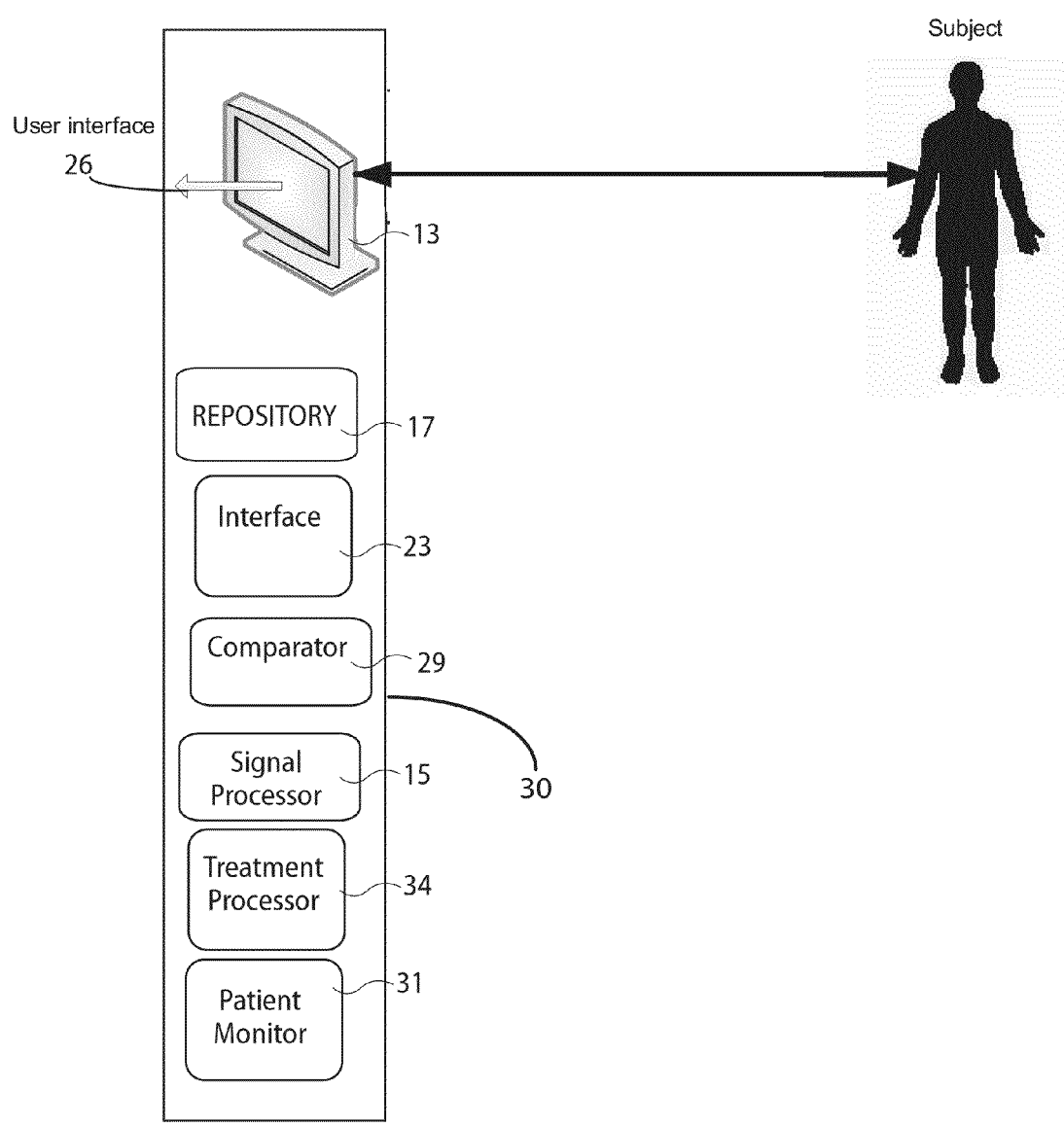
FIG. 1 shows a system for heart performance characterization and abnormality detection, according to invention principles.

A system improves detection of cardiac atrial electrophysiological activities, by analyzing atrial electrophysiological signals (including surface ECG signals and intra-cardiac electrograms) in response to fast and slow atrial rotor activity data extraction within a P wave signal portion, for example. The system quantifies signal waveform changes within atrial electrophysiological signals, especially in atrial multi-rotor component signals to provide an accurate time of event occurrence, atrial arrhythmia type, abnormal excitation rotor location and atrial pathology severity for improved diagnosis, such as of atrial fibrillation arrhythmia. In one embodiment the system employs atrial subcomponent (rotor activity) signal related calculation for identifying atrial tissue and rhythm disorders, differentiating between cardiac arrhythmias, characterizing pathological severity, predicting life-threatening events, and evaluating drug delivery effects. The system is usable for cardiac condition detection, such as of myocardial ischemia, ventricular tachycardia, and ventricular fibrillation.

The system provides continuous atrial arrhythmia detection and characterization using atrial sub-level component signal analysis as qualitative and quantitative indications for early accurate detection of atrial arrhythmias. In response to occurrence of certain abnormality or clinical events, cardiac tissue is affected and a pacing excitation conduction mechanism is impacted with nonlinear abnormal variations. Electrophysiologically, there is more than one atrial excitation rotor within an atrial chamber and tissue. Usually, in an early stage of atrial arrhythmias, irregularity is less than that in a later stage.

A system provides atrial signal and activity acquisition, sub-level component signal extraction, atrial arrhythmia analysis and characterization, such as of severity and indicates treatment priority. Atrial electrophysiological signals and activities, including atrial depolarization and repolarization (from the onset of a P wave to peak of an R wave not just a P wave), are separated and decomposed into different amplitude components in the time domain. The system advantageously associates different components with different atrial rotors in atrial chamber electrophysiological signals and uses the components to assess the relative significance of the rotors for determination of treatment (e.g. ablation targets and priority). The system advantageously determines and quantifies the multi atrial rotors in the atrial signals and activities. Different sub-level amplitude components in the decomposition represent different rotors in the atrium. The characteristics and number of the rotors reflect the atrial functionality and abnormality. By analyzing the sub-level amplitude components (rotor components), the system determines rotor location and time of abnormal event occurrence and treatment priorities, such as ablation sequence, stimulation or medication are determined. For example, from normal heart rhythm to atrial fibrillation or atrial flutter, the number of atrial rotors in the chamber may increase, which mean abnormal additional rotors emerge and may affect the electrophysiological activities, such as excitation conduction. Additionally the rotor component characteristics, such as energy and amplitude are also used to detect changes for atrial fibrillation detection and characterization.

A rotor is defined herein as a propagating wave of excitation in a heart. Electrophysiological signals are derived in response to a combination of action potentials of myocardial cells in cardiac tissue. Heart tissue excitation is electrical conduction between different portions of heart, e.g. from different portions of tissue in the same chamber, and from chamber to chamber (such as from atrium to ventricle). An excitation wave is elicited at the excitable site that is in the form of a rotor in the cardiac tissue. The rotor has a marked curvature and this curvature shows the propagation and excitation of the electrophysiological pattern in the cardiac muscle. From normal healthy heart excitation to abnormal (such as arrhythmia) rhythm, there may be abnormal rotors and electrophysiological activities in the heart, which lead to cardiac function irregularity termed pathology and arrhythmia. The system analyzes rotor activities and characteristics (such as their number, energy) including location, timing and severity for cardiac pathology monitoring and diagnosis.

FIG. 1 shows system 10 for heart performance characterization and abnormality detection. System 10 comprises at least one computer system, workstation, server or other processing device 30 including, reproduction device 13, repository 17, signal processor 15, interface 23, comparator 29, treatment processor 34, patient monitor 31 and a user interface 26. Interface 23 receives sampled data representing an electrical signal indicating electrical activity of a patient heart over multiple heart beat cycles. Signal processor 15 automatically decomposes the received sampled data to multiple different subcomponent signals in the time domain. Processor 15 associates individual decomposed subcomponents with corresponding different cardiac rotors and determined characteristics of the subcomponents indicating relative significance of the rotors in a cardiac atrial condition. Reproduction device 13 includes user interface 26 for providing data indicating the subcomponent characteristics indicating relative significance of the rotors in a cardiac atrial condition.

Treatment processor 34 automatically provides data indicating treatment suggestions in response to the data indicating relative significance and anatomical location of the rotors. Comparator 29 compares at least one of the subcomponent characteristic values or a value derived from a subcomponent characteristic value with a threshold value to provide a comparison indicator. Patient monitor 31 in response to the comparison indicator indicating a calculated subcomponent characteristic value exceeds the threshold value, generates an alert message associated with the threshold. Repository of data 17 stores received sampled data representing an electrical signal indicating electrical activity of a patient heart over multiple heart beat cycles, decomposed multiple different subcomponent signals in the time domain, determined characteristics of the subcomponents indicating relative significance of the rotors and treatment suggestions. User interface 26 provides a display for presentation of alert messages and determined signal parameters.

Figure 2:
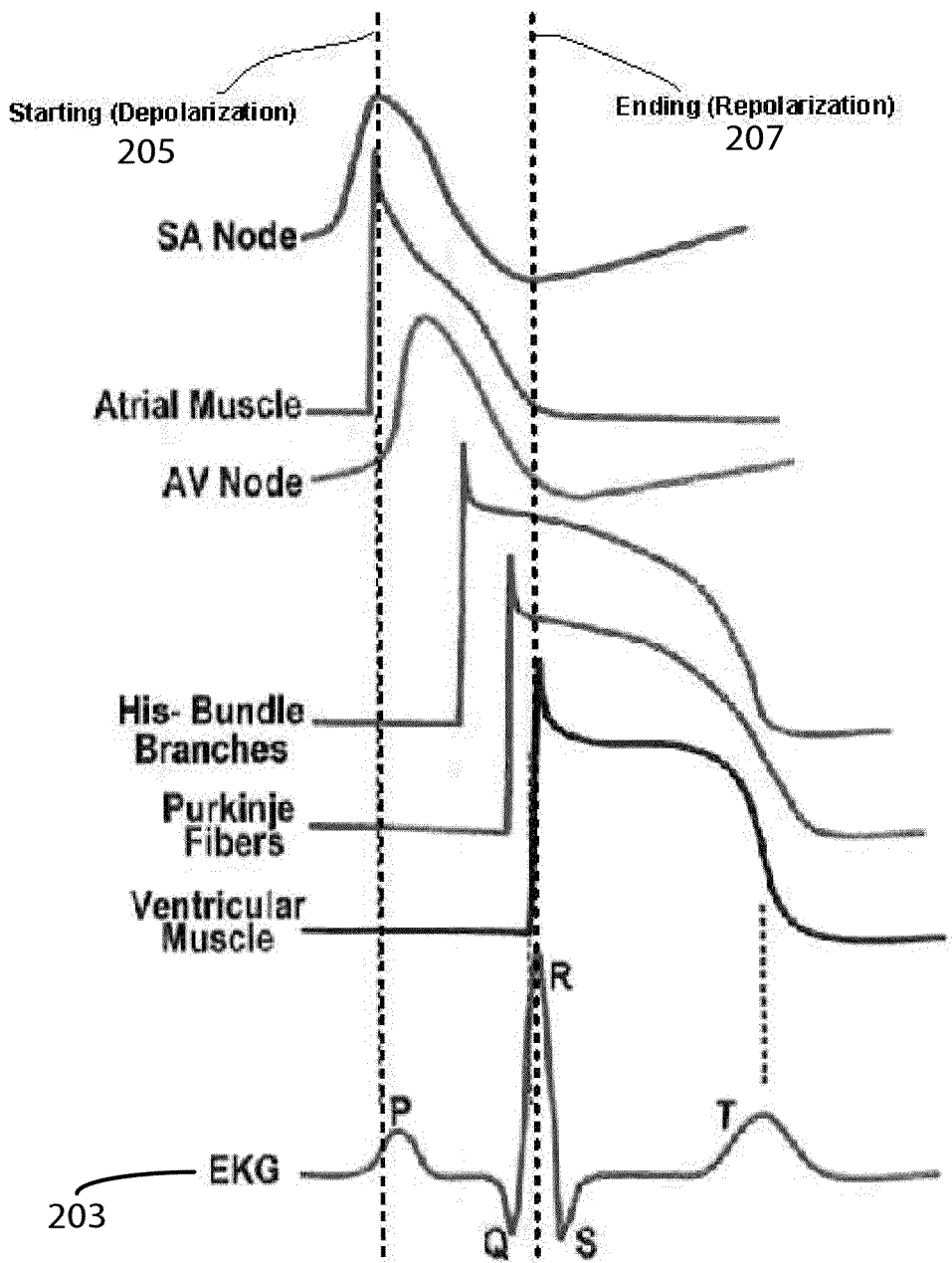
FIG. 2 shows electrophysiological signals and responses from different portions of cardiac tissue and chambers.

FIG. 2 shows electrophysiological signals and responses from different portions of cardiac tissue and chambers. Atrial activities can be divided into two portions: depolarization and repolarization. A user analyzes a depolarization (P wave) signal amplitude and waveform morphology and shape, to detect and characterize atrial abnormality and events. However atrial muscle function related activity is not exclusively confined to a P wave portion. Further, repolarization activity may extend to a QR wave portion. An electrophysiological response is shown for different portions of heart EKG/ECG signal 203. The period of time from onset of the P wave to the beginning of a QRS complex is termed a P-R interval, which normally ranges from 0.12 to 0.20 seconds in duration. This interval represents the time between the onset of atrial depolarization and the onset of ventricular depolarization. A P wave is a depolarization portion of atrial function. The repolarization may affect additional information in an ECG signal, such as a PQ portion and a QR portion (30-120 mS). In order to more accurately characterize changes in atrial tissue, system 10 analyzes a waveform from onset of P wave to R wave which includes both atrial depolarization and repolarization procedures.

Timing of atrial response and electrophysiological signals is from early P wave 205 to R wave 207. Atrial activities comprise a combination of fast wave and slow wave activity (response) portions, which may not track small ECG signal changes and early atrial arrhythmias. For example, in some atrial arrhythmias, such as AF (there are multiple rotors in the atrium which may delay the atrial response and impact ECG signal construction and distribution), the frequency, energy and combination ratios of a fast wave and slow wave are usually affected and can be used to achieve early detection of arrhythmias. System sub-level component analyses of the atrial electrophysiological activities are advantageously used to detect and characterize atrial tissue and function variations.

Figure 3:
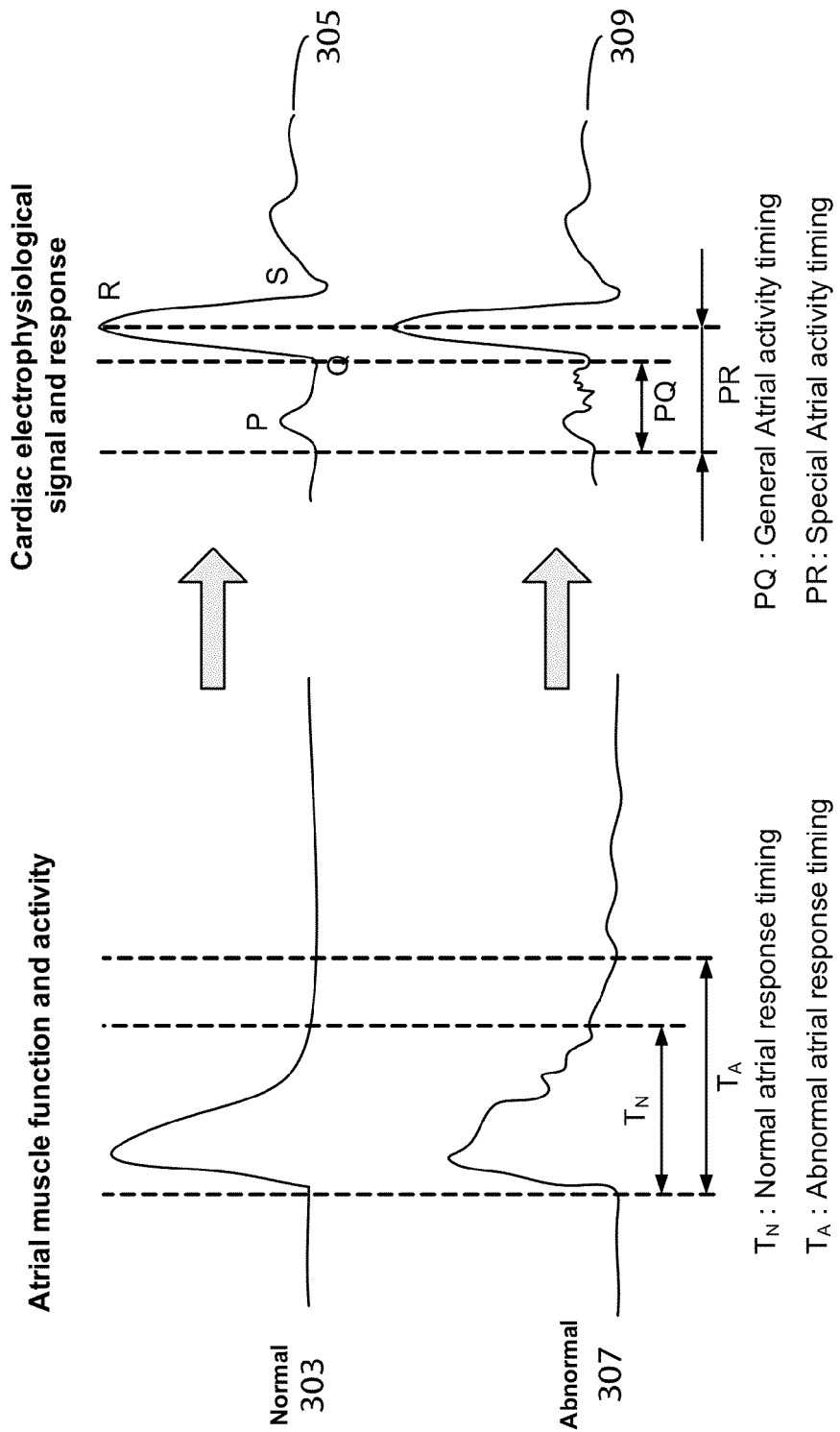
FIG. 3 shows comparison of morphology and timing of atrial muscle and cardiac electrophysiological signals (such as surface ECG, intra-cardiac electrograms), according to invention principles.

FIG. 3 shows comparison of morphology and timing of atrial muscle and cardiac electrophysiological signals (such as surface ECG, intra-cardiac electrograms). Specifically, FIG. 3 shows atrial function 303, 307 and corresponding electrophysiological response 305, 309 in normal and abnormal cases. During abnormal (atrial arrhythmia) cases, the atrial response is partially delayed and the whole atrial activity time is prolonged, which indicates there are different rotors in the atrial tissue and chamber. In comparison with normal cardiac signal waveform and atrial electrophysiological response, an abnormal signal may have longer activity timing, more frequency waveform subcomponents (due to different exciting motors) in the signal morphology and different ratios between atrial sub-level components, due to the atrial arrhythmias. The subcomponents (atrial rotors) facilitate determination and characterization of atrial signal changes and atrial event information.

Different methods may be used for atrial signal waveform decomposition and component analyses, including spectral peak frequency component analysis, ICA (independent component analysis), PCA (principal component analysis), for example. However these methods may not be able to extract different rotor information associated with a fast wave and a slow wave rotor, for example. In one embodiment, system 10 (FIG. 1) uses empirical mode decomposition (EMD) and component analysis to extract and separate subcomponents within atrial and electrophysiological response signals. Fast and slow atrial rotor activity data extraction and calculation concerning an atrial activity signal portion are utilized to determine and characterize atrial arrhythmias. System 10 detects and characterizes atrial arrhythmia, such as an early AF event, by analyzing a ratio of different subcomponent energy values, a ratio of dominant frequency of different rotor components, or another user defined ratio of subcomponents of atrial tissue function signals. This reduces patient risk (such as of ablation and electrical shock), improves successful rate of treatment (early detection and treatment saves lives), and lowers clinical cost and complexity.

Figure 4:
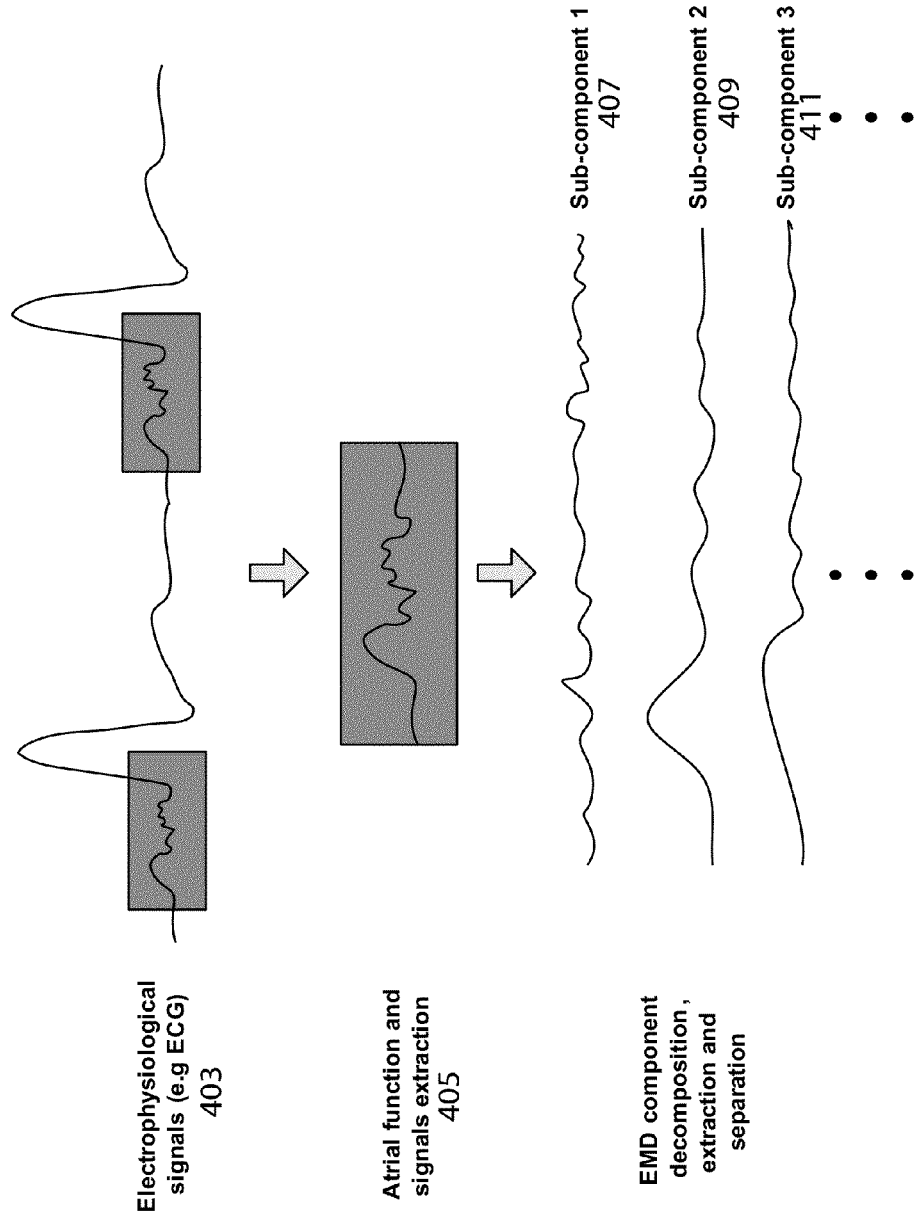
FIG. 4 shows empirical mode decomposition (EMD) method based atrial signal separation and sub-level component extraction, according to invention principles.

FIG. 4 shows empirical mode decomposition (EMD) method based atrial signal separation and sub-level component extraction. An EMD method 405 is used to obtain decomposed signal components 407, 409, 411, which may come from a recorded electrophysiological signal 403 of a patient and the system determines ratios of the determined subcomponents. The known EMD decomposition method is described in the Appendix in connection with FIG. 12 and separates fast and slow waveform rotors within atrial function signals and waveforms. System 10 performs atrial subcomponent decomposition by cardiac signal sampling and acquisition, atrial signal filtering and EMD based subcomponent decomposition and separation involving N levels of derived components where N is determined in response to user command. The subcomponent decomposition separates an atrial signal into different fast and slow rotor components comprising different excitation subcomponents. The subcomponents are used to track, analyze and characterize small signal changes (often invisible in an overall signal, such as a surface ECG signal or intra-cardiac electrogram) indicating rotor component changes. In contrast known frequency band separation may fail to extract different fast and slow rotor components from electrophysiological signals which may have a broad frequency band.

In the example of FIG. 4, there are N level derived subcomponents which are decomposed by an EMD function. N is a number of total subcomponents, determined by a user or adaptively by the system. An atrial activity signal S, upon EMD separation comprises N level components: $C_1, C_2, \ldots, C_N$, therefore, $$S = \sum_N C_i, \text{ and}$$

$$\text{Energy}(C_N) = \sum_{C_{N_j} \in C_N} |C_{N_j}| < \delta \% \cdot |S|$$

Where, $C_i$ is a subcomponent of i level derived from EMD component extraction. In each level, a subcomponent is a series of data comprising a dataset; for example, in level N, the subcomponent $C_N$ is a data series of $c_{N_j}$; $\delta\%$ controls the N level decomposition, for example assuming $\delta\%$ is 1%, it means the decomposition procedure is complete if energy of the total data series of the subcomponent $C_N$ is less than 1% of the total signal S.

Figure 5:
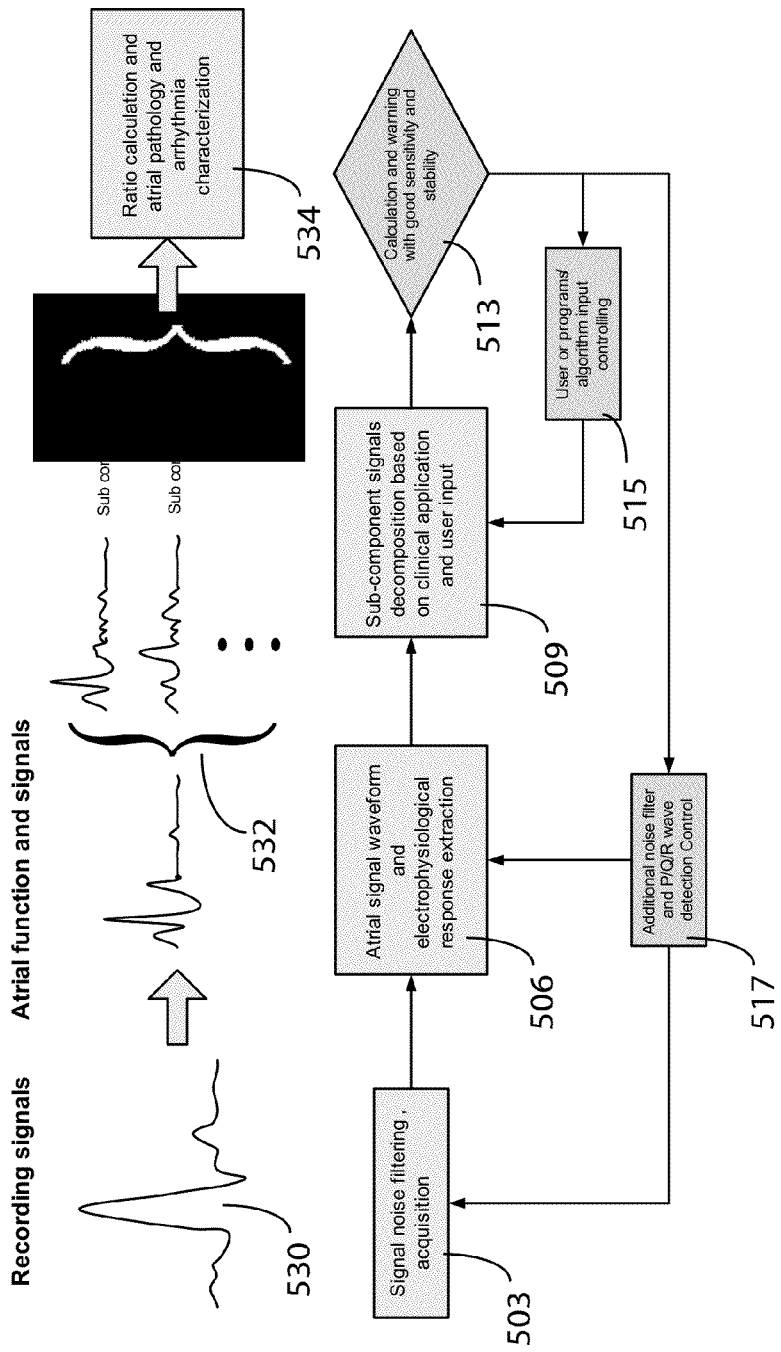
FIG. 5 shows atrial signal extraction and subcomponent separation and diagnosis, according to invention principles.

FIG. 5 shows atrial signal extraction and subcomponent separation and diagnosis using control and calculation modules for identifying different sub level components. In response to signal noise filtering and atrial function extraction, the atrial waveforms are decomposed into multiple subcomponents which are analyzed to derive ratios for atrial arrhythmia and event detection. Unit 503 acquires and filters heart electrical activity signal data 530 using high, low and bandpass filters and choke (cancelling common mode noise) filters. Unit 506 performs first level cardiac signal extraction on filtered signal 530 to determine atrial electrophysiological activity and timing, involving P wave detection, RR wave detection and Q wave detection. Unit 509 performs second level subcomponent signal decomposition on the determined first level atrial electrophysiological activity data in response to user or system input 515, to extract and separate sub-level components 532 and atrial rotors for further component ratio analysis. Unit 513 calculates a ratio 534 for atrial arrhythmia diagnosis and characterization, such as of AF and atrial flutter in atrium tissue. Unit 517 adaptively changes filter configuration and P, Q, R wave segment detection thresholds in response to calculated ratios to improve signal feature detection. Unit 513 advantageously identifies and associates subcomponents with cardiac rotors as shown in the Table of FIG. 6 according to fast and slow atrial rotors, for example.

FIG. 6 shows a table of extracted sub-level component signals identified in column 605 (component C1, C2, C3, C4, C5) corresponding to atrial electrophysiological activity described in column 607 (e.g., C1 is fast rotor component 1, C2 is fast rotor component 2, C3 is middle rotor component). The number (N) of sub level components depends on user or system control. A typical atrial signal extraction may use a value of N=5, which means a $6^{th}$ component and the rest of the subcomponents are small. But the number of components in the atrial signal extraction and decomposition depends on clinical application (e.g., AF detection, atrial function monitoring).

Figure 7:
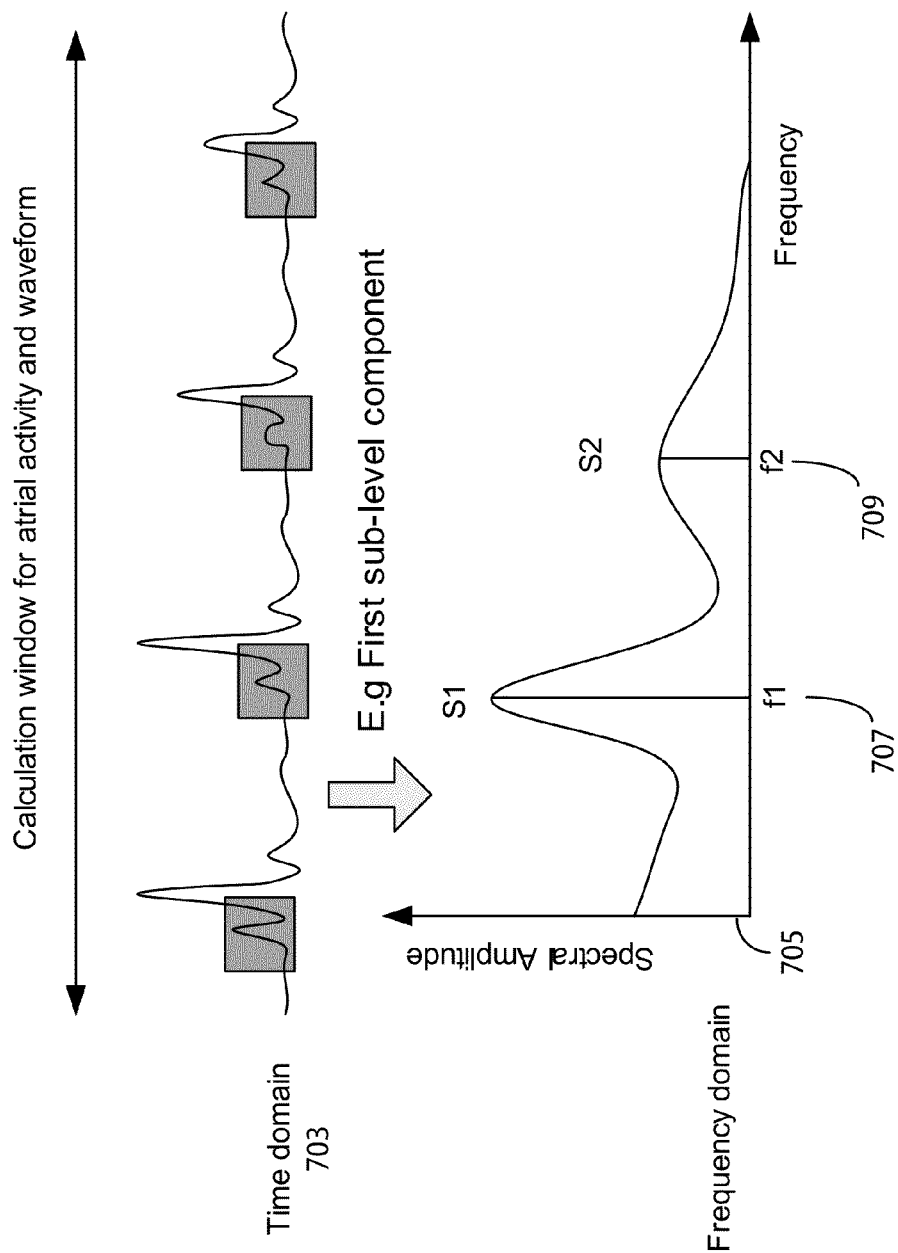
FIG. 7 illustrates time and frequency domain signal distribution for an atrial waveform and electrophysiological response, according to invention principles.

FIG. 7 illustrates time and frequency domain signal distribution for an atrial waveform and electrophysiological response. Spectral analysis is performed for each subcomponent signal of an atrial electrophysiological signal. As shown in the Figure, the energy of each subcomponent, the dominant frequency of each subcomponent, and different frequency peaks within a subcomponent signal, are determined. The system performs windowed multi-cycle based signal variation and variability analysis in the time domain for mode and pattern change identification. In the frequency domain, the highest peak in the spectrum and peak frequency in one embodiment are used for detecting, analyzing and characterizing cardiac atrial tissue and function changes. Time domain curve 703 shows an extracted, filtered first subcomponent C1 in the time domain indicating atrial activity in a ROI used for atrial arrhythmia analysis. Plot 705 shows spectral amplitude versus frequency of the first subcomponent 703 comprising a spectrum analysis. Plot 705 illustrates a spectrum distribution in the frequency domain of C1 including components 707 and 709. In an individual cardiac atrial cycle, a ROI can be derived from an averaged electrophysiological signal derived by averaging the signal over multiple heart cycles to reduce effects of system noise and patient artifacts. The frequency f1 707 is a dominant frequency of first subcomponent C1 in the atrial electrophysiological signal and comprises a frequency value of a maximum peak in the spectral distribution.

The system uses an N level EMD component decomposition of an atrial electrophysiological signal to provide components associated with atrial excitation rotors. The system calculates ratios for signal analysis including, a) an atrial subcomponent portion signal Energy ratio $$\text{Ratio\_C}_i = \frac{\text{energy}(C_i)}{\text{energy}(S)}$$

where $$\text{Energy}(C_i) = \sum_{C_{i_j} \in C_i} |C_{i_j}|;$$

$C_i$ is a subcomponent of i level derived from EMD component extraction; in each level, a subcomponent is a series comprising a dataset; Ratio\_$C_i$ stands for an energy portion of number #i sub level component (excitation rotor) in an atrial electrophysiological signal.

b) a subcomponent comparison energy ratio $$\text{Ratio\_C}_{mn} = \frac{\text{energy}(C_m)}{\text{energy}(C_n)}$$

where, energy($C_m$) and energy($C_n$) represent an energy calculation of a sub-level component $C_m$ and $C_n$; the subcomponent comparison energy ratio Ratio\_$C_{mn}$ illustrates an energy distribution between the excitation rotor activities within an atrial signal over a heart cycle.

c) an atrial sub-level component signal dominant frequency ratio $$\text{Ratio\_dominant\_freq\_C}_{mn} = \frac{\text{dominant\_freq}(C_m)}{\text{dominant\_freq}(C_n)}$$

where do min ant\_freq($C_m$) and do min ant\_freq($C_n$) represent a dominant frequency value of sub-level component $C_m$ and $C_n$; Ratio\_do min ant\_freq\_$C_{mn}$ illustrates a main frequency shift between sub-level components within an trial function signal. The variation and changes of this ratio are used to detect small changes within atrial rotors.

d). atrial sub-level component signal frequency ratio $$\text{Ratio\_freq\_distribuion\_C}_i = \frac{\text{First\_max\_frequency}(C_i)}{\text{Second\_max\_frequency}(C_i)}$$

where, First\_max\_frequency($C_i$) and Second\_max\_frequency($C_i$) represent values of a first maximum peak and second maximum peak frequency within a spectrum distribution comprising sub-level component $C_i$. The Ratio\_freq\_distribution\_$C_i$ illustrates a frequency shift and complexity change inside an atrial excitation rotor. If changes in a rotor are determined and tracked, the distortion and changes in atrial functionality may be characterized and quantified.

The system employs statistical evaluation methods to quantify and characterize calculated parameter change for categorization of atrial arrhythmia severity. The system performs atrial signal ratio characterization using ratio combination, $$\text{Atrial component ratio}: \Re_{Atrial} = \sum_{i \in ratio\_combination} \gamma_i(t)\mu_i$$

where, i is the number of an atrial sub-level component function ratio as previously described; $\mu_i$ is the ratio which may be selected from energy portion ratios, energy comparison ratio, dominant frequency ratios, $s\delta_i(t)$ is a weight for each ratio in the combination calculation and $\mu_i$ may be programmable and time varying and adaptively updated by a user or the system. Atrial component ratio $\Re_{Atrial}$ value may be utilized for different kinds of atrial arrhythmia detection, diagnosis and characterization, such as atrial fibrillation and flutter event detection and evaluation. For example, it can be utilized to detect and characterize AF event occurrence and AF event severity, to predict a critical time of an atrial event and treatment (such as medication, treatment time).

The system employs statistical calculations for atrial electrophysiological arrhythmia characterization including, $$\text{Mean or average value (expectation); mean}(X) = \frac{1}{N}\sum_{i \in N} X(i);$$

$$\text{Standard deviation} STD(X) = \frac{1}{N-1}\sum_{i \in N-1}(X(i) - \text{mean}(X))$$

$$\text{Signal Variation Vary }(X) = \frac{\text{mean}(X)}{STD(X)}$$

$$\text{Signal Variability Verb} = \frac{\max(X - \text{mean}(X))}{\text{mean}(X)}$$

where, X is an atrial signal waveform parameter such as an atrial subcomponent energy ratio or dominant frequency ratio; N is a calculation window size (there are N heart beat cycles in a shifting calculation window where a heart cycle is determined from a surface ECG or intra-cardiac electrogram signal). The system also performs a high order statistical calculation (HOS), test methods such as a t-test and hypothesis evaluations of the signal and data distribution.

Figure 8:
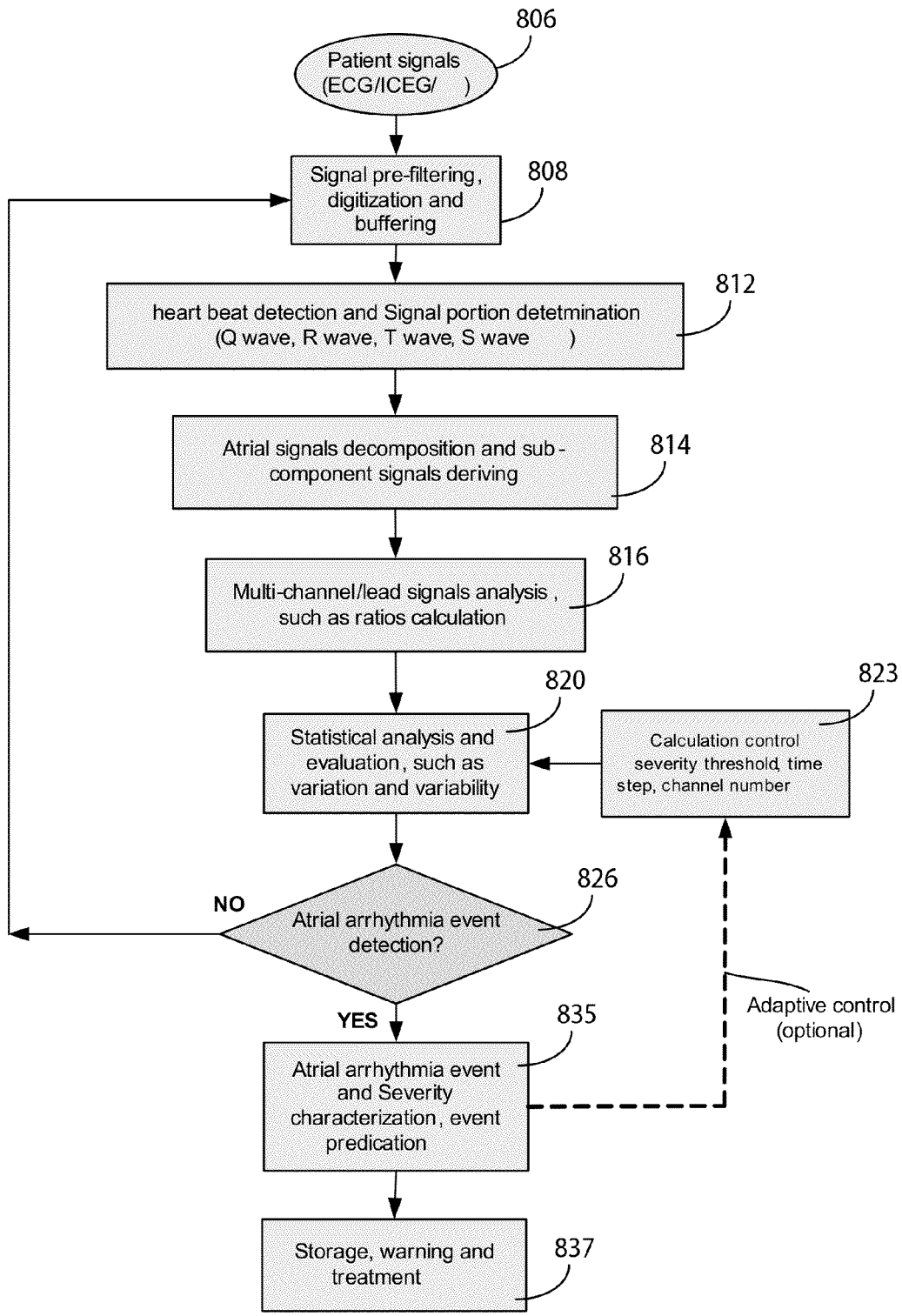
FIG. 8 shows a flowchart of a process for calculation, monitoring and characterizing atrial function and activity status based on atrial waveform signal and subcomponent ratios, according to invention principles.

FIG. 8 shows a flowchart of a process performed by system 10 (FIG. 1) for calculation, monitoring and characterizing atrial function and activity status based on atrial waveform signal and subcomponent ratios. Signal processor 15 buffers, filters and digitizes an ECG (or ICEG) signal in step 808 received in step 806. Processor 15 in step 808 filters the received signal data using a filter adaptively selected in response to data indicating clinical application to remove patient movement and respiratory artifacts as well as power line noise. In step 812, processor detects P wave, Q wave, R wave, T wave, S wave and U wave segments of the filtered received signal data by detecting peaks within the received data using a known peak detector and by segmenting a signal represented by the received data into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

In step 814, processor 15 decomposes a ROI (region of interest) of an atrial signal into multiple subcomponents in the time domain using EMD or another decomposition method such as ICA, PCA, and wavelet signal component analysis. Processor 15 associates individual decomposed subcomponents with corresponding different cardiac rotors and determined characteristics of the subcomponents indicating relative significance of the rotors in a cardiac atrial condition. Signal processor 15 in step 816 performs atrial waveform and electrophysiological waveform decomposition into subcomponents for signals acquired on multiple different leads of a multi-lead catheter comprising different channel cardiac signals having different sensitivities, for example. Processor 15 also calculates the subcomponent energy and dominant frequency ratios previously described. Processor 15 calculates the previously described Atrial component ratio $\Re_{Atrial}$. In step 820 processor 15 performs a statistical analysis and characterization of the calculated atrial signal ratios and parameters by determining standard deviation, variability and variation.

If signal processor 15 in step 826, using baseline values and thresholds identifies a medical condition such as an atrial arrhythmia event or another abnormality, processor 15 in step 835 uses mapping information, associating ranges of sub-component values and values derived from the subcomponent values with corresponding medical conditions in determining severity, type and location of a cardiac condition. The mapping information associates the ranges with particular patient demographic characteristics and with corresponding medical conditions. Processor 15 uses patient demographic data including at least one of, age, weight, gender and height in comparing a characteristic value with the ranges and in step 837 generates an alert message indicating a potential medical condition and stores data indicating the identified condition and associated calculated parameters in repository 17. Processor 15 in step 823 adaptively selects a signal channel, adjusts a time window as well as window shift step, the number of samples in a calculation window used for calculation and adjusts the selected portions and ROI of a filtered signal and adjusts a threshold employed by processor 15 to improve medical condition detection. If signal processor 15 in step 826 does not identify a medical condition, the process is repeated from step 808.

Figure 9:
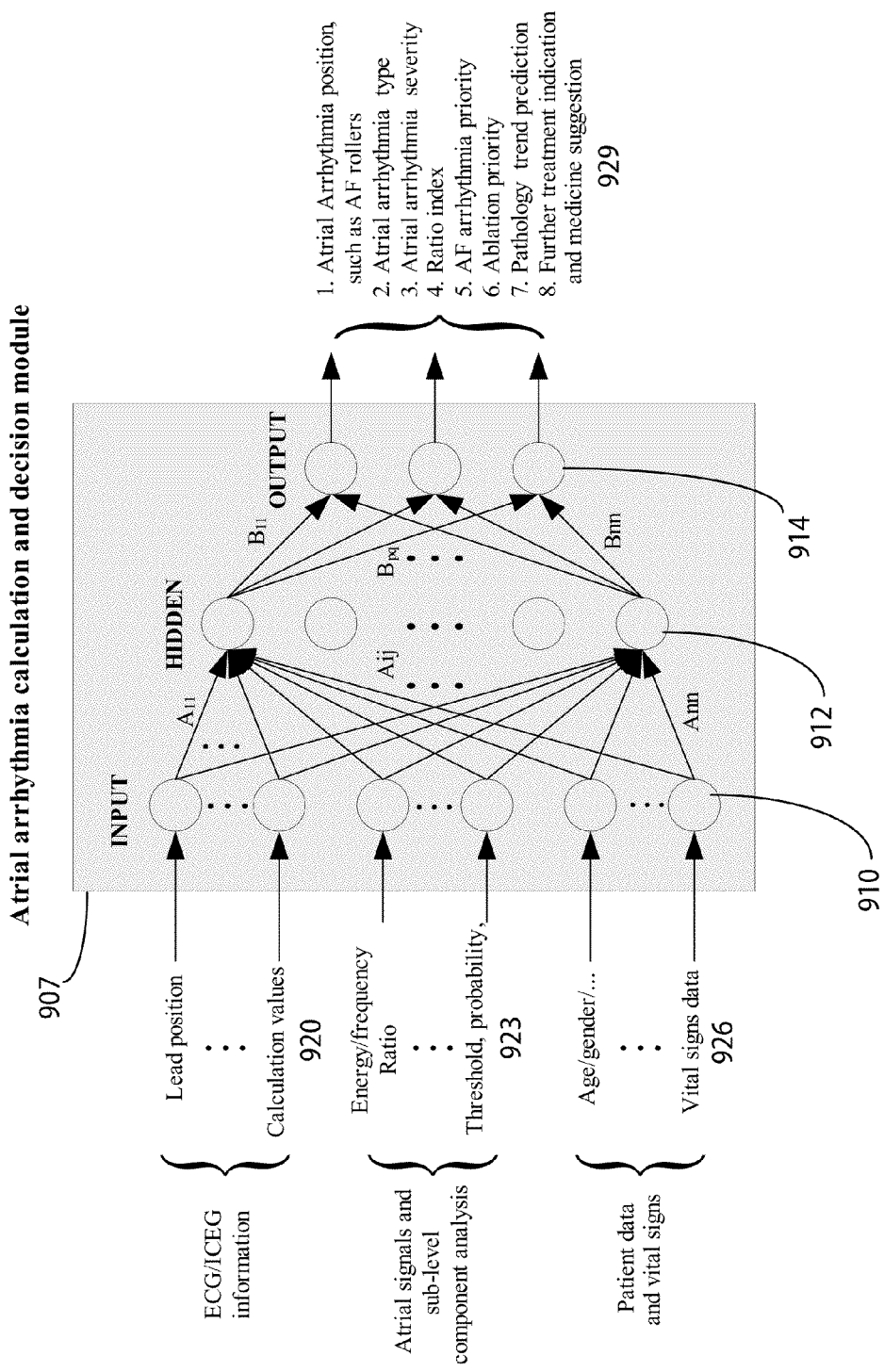
FIG. 9 shows an artificial neural network (ANN) unit for atrial arrhythmia detection and heart function analysis, according to invention principles.

FIG. 9 shows an artificial neural network (ANN) unit 907 for atrial arrhythmia detection and heart function analysis. The system ratio analysis and calculated parameters may be combined to analyze patient atrial arrhythmias and to determine health status, pathology and event trends. Different methods may be used for multi-channel analysis, such as a Fuzzy system or expert system. An ANN based comprehensive decision analysis is utilized for multi-channel and multi-parameter/calculation based patient monitoring. ANN unit 907 integrates and nonlinearly combines multiple kinds of patient information since different types of patient data and data patterns may have a nonlinear relationship. ANN unit 907 comprises a three layer architecture for combining and integrating different kinds of patient information, such as ECG or ICEG multi-channel signals (such as from a multi-lead intra-cardiac catheter) 920 and signals derived by atrial subcomponent analysis including energy, dominant frequency ratios and thresholds 923 and patient data including age, gender and vital sign parameters 926. In this way, the severity, type, trend, of the ongoing atrial arrhythmias are detected. The system quantifies atrial pathologies and events, which facilitates diagnosis of treatment methods, such as ablation point priorities, ablation energy, ablation timing, patient treatment evaluation. For example, in AF treatment, a user is provided with a mapping and analysis structure of an atrial chamber. This facilitates treatment and reduces risk and complexity of a treatment procedure.

ANN unit 907 combines and maps parameters 920, 923 and 926, to output parameters 929. The output parameters 929 indicate atrial arrhythmia position, type, severity and relative priority for treatment, calculated ratios, pathology trend and suggested treatment and medication. ANN unit 907 structure comprises 3 layers, an input layer 910, hidden layer 912 and output layer 914. ANN unit $A_{ij}$ weights are applied between input layer 910 and hidden layer 912 components of the ANN computation and $B_{pq}$ weights are applied between hidden layer 912 and calculation components 914 of the ANN computation. The $A_{ij}$ weights and $B_{pq}$ weights are adaptively adjusted and tuned using a training data set. ANN unit 907 incorporates a self-learning function that processes signals 920, 923 and 926 to increase the accuracy of calculated results.

ANN unit 907 maps input signals 920, 923 and 926 to a candidate diagnosis or treatment suggestion 929 to localize tissue impairment within an organ and determine time of occurrence within a heart cycle. The ANN based atrial signal and response control and adjustment combines signal analysis results, patient history and physician experience (input data and control) which reduces risk to patient heart tissue from over-pacing, tissue burning. The ANN based calculation and decision module 907 provides detection, localization, characterization and prediction of the location of atrial abnormnnality, severity of the atrial arrhythmia, effectiveness of an ablation sequence and priorities in an atrial chamber and tissue.

Figure 10:
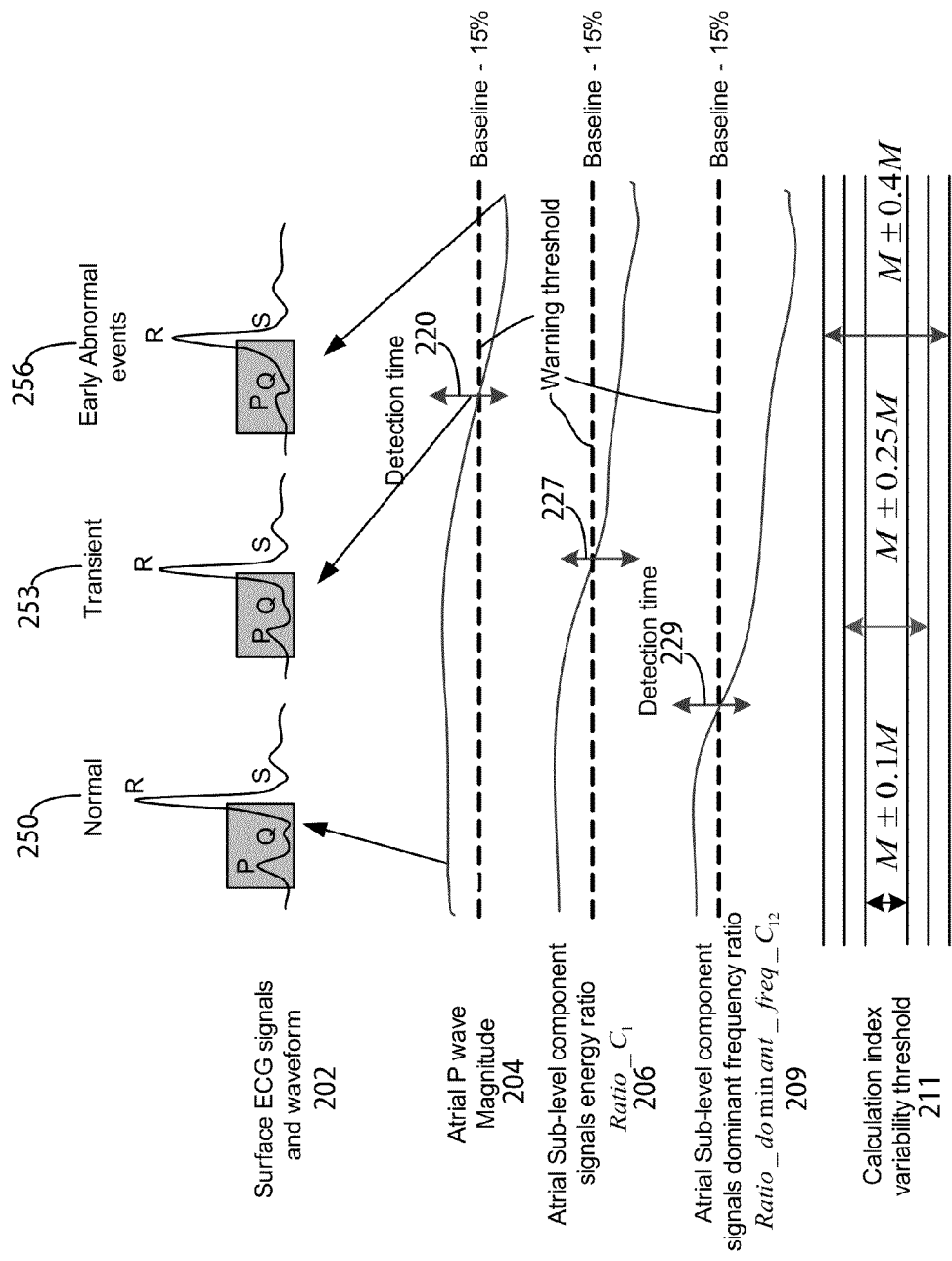
FIG. 10 shows an example of atrial fibrillation and activity analysis based on atrial sub-level component extraction, characterization and ratio analysis, according to invention principles.

FIG. 10 shows an example of atrial fibrillation and activity analysis based on atrial sub-level component extraction, characterization and ratio analysis. Atrial signal subcomponent analysis, rotor separation and ratio calculation is utilized to monitor and diagnose different kinds of clinical events and cardiac pathologies in an atrium, such as atrial fibrillation, atrial flutter. A single channel surface ECG lead (Lead I) signals 202 shows an atrial fibrillation simulation involving normal 250, transient 253 and atrial fibrillation (arrhythmia) 256 stages. Different calculated parameters are compared, including P wave amplitude magnitude 204 of original ECG waveform 202, atrial energy ratio 206 and atrial dominant frequency ratio 209 for severity of atrial pathology and event quantification, for example. Signal processor 15 (FIG. 1) uses a calculation variability threshold (predetermined baseline and warning threshold) analysis to identify and characterize acute small changes within atrial signals. A 10-heart-beat window size is used for averaging to obtain a mean and standard deviation value for a calculated parameter, such as timing and ratios, for example. Normal signals are used as a reference and baseline in the calculation.

Subcomponent analysis of atrial signal 202 involves determination of P wave amplitude magnitude 204, the energy ratio of the first subcomponent C1 206, and the cross ratio of the dominant frequency ratio Ratio_do min ant_freq_$C_{12}$ 209. Subcomponents are derived by using EMD separation and component decomposition. For each cardiac cycle or shifting time step, a calculation is performed to characterize the atrial signal component changes. In this simulation example, signal 202 shows change from a normal healthy heart beat 250 through a transient heart beat 253, to an early atrial arrhythmia 256 (early stage of the AF). The normal healthy heart beat in the early portion of the data series is selected as a baseline (or benign signal) for comparison and normalization, to show changes as a percentage in three calculated parameters 204, 206 and 209. The P wave amplitude magnitude 204 shows that relative change of a P wave amplitude drops more than 15% 220 at the early stage of the arrhythmia. The corresponding P wave amplitude magnitude for the three stages (healthy, transient and early AF) are 100%, 95% and 82% respectively. Arrows 220, 227, 229 show the detection time point corresponding to the 15% threshold (the threshold is adaptively dynamically changed as illustrated by values 211 by the system or a user).

Compared with P wave magnitude changes, the energy ratio 206 and dominant frequency ratio 209 of the subcomponents of the atrial activities show better results and give an earlier detection time with improved change detection sensitivity and reliability. The energy ratio Ratio_$C_1$ 206 calculation of the data series for the three stages (episodes) indicates 100%, 84% and 72% change in comparison with the normal healthy heart beat. The Ratio_$C_1$ calculated value 206 shows a 15% drop in value 30 seconds earlier than the P wave amplitude magnitude 204 (the threshold is set the same as P wave amplitude magnitude, 15%). The atrial subcomponent dominant frequency ratio Ratio_do min ant_freq_$C_{12}$ 209 is calculated and the ratio results are 100%, 81% and 58% respectively for healthy heart beat, transient heart beat and early AF stages. Compared with Ratio_$C_1$ calculation, the Ratio_do min ant_freq_$C_{12}$ shows an earlier detection time, at about 12 seconds earlier than the Ratio_$C_1$ calculation. The calculation method is selected and determined by a user or automatically by the system in response to data identifying clinical application and factors such as sensitivity ratio, reliability of calculation, window size used for averaging, calculation time step and warning threshold.

Figure 11:
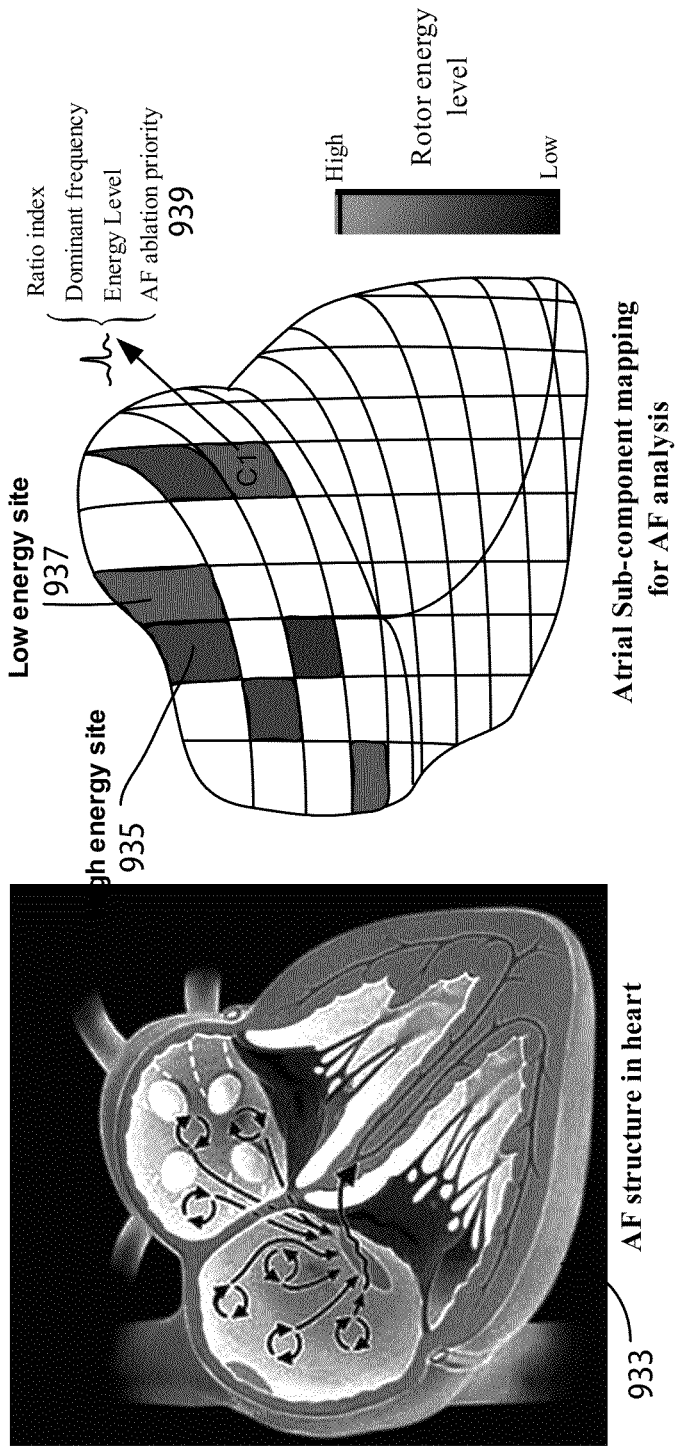
FIG. 11 shows multi-channel electrophysiological signal based AF localization and mapping, according to invention principles.

FIG. 11 shows multi-channel electrophysiological signal based AF localization and mapping based on energy ratio Ratio_$C_1$ of a first subcomponent of an atrial electrophysiological signal. The 2D or 3D atrial subcomponent signal and related calculation mapping is associated with an event combination comprising a P wave magnitude, energy ratio and dominant frequency parameters. The heart diagram 933 shows rotors associated with determined subcomponents. Data from each available lead or site in an atrial chamber is filtered, decomposed and processed to provide subcomponent parameters and associated ratios. The calculated subcomponent parameters are mapped in 2D or 3D in real time to tissue locations such as locations 935 (a high energy rotor site) and 937 (a low energy rotor site) and the mapping is updated at a calculation interval time step repetition rate. Signal processor 15 uses the mapping and subcomponent energy, dominant frequency and ratios (e.g. 939) in a heart structure in characterizing atrial chamber sites at a lead location and identifies an abnormal atrial rotor and changes in atrial rotor activity. This facilitates determination of a correct treatment, including ablation priority, ablation energy, ablation timing, ablation location.

Figure 13:
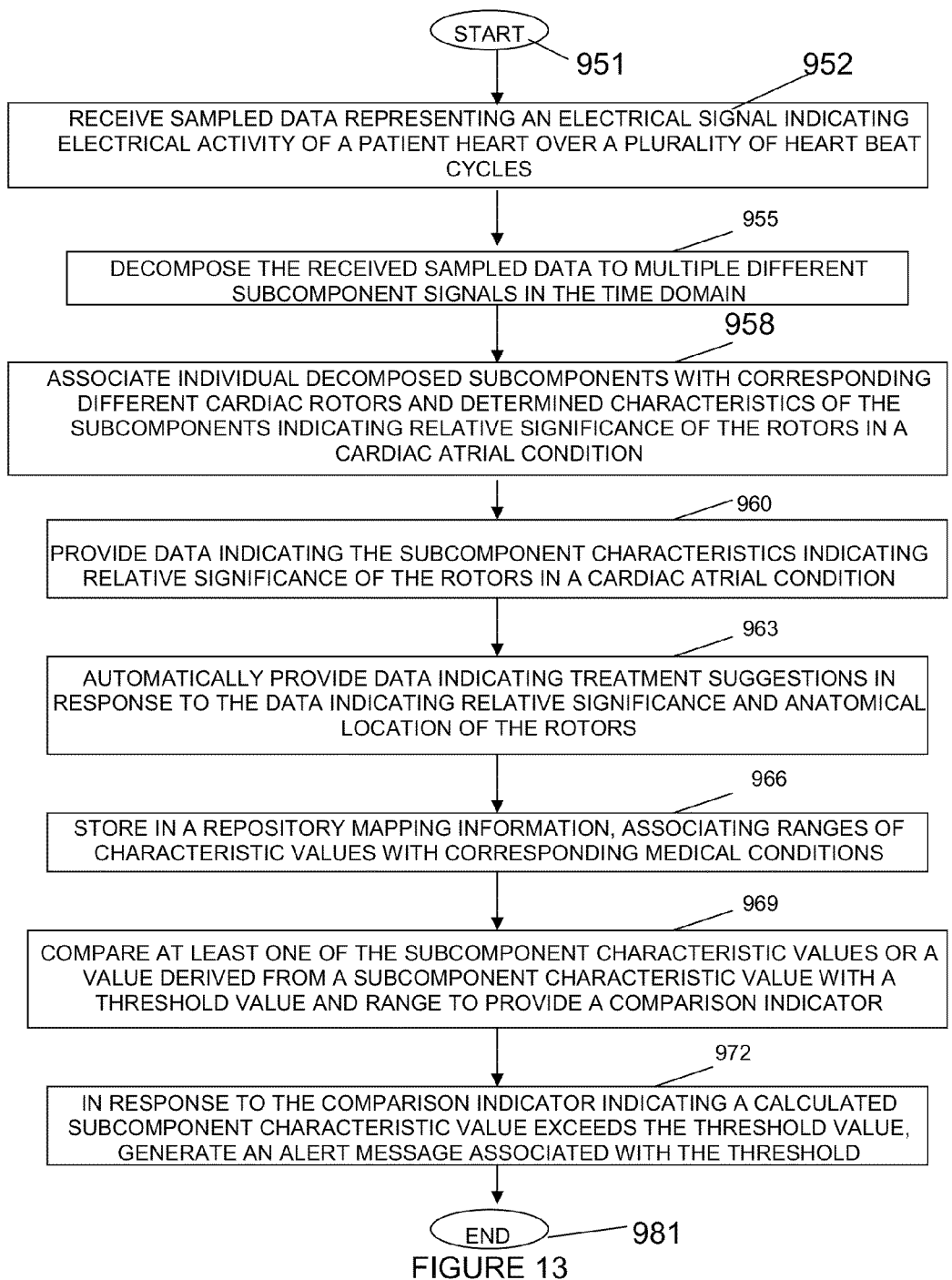
FIG. 13 shows a flowchart of a process used by a system for heart performance characterization and abnormality detection, according to invention principles.

FIG. 13 shows a flowchart of a process used by system 10 (FIG. 1) for heart performance characterization and abnormality detection. In step 952 following the start at step 951, interface 23 receives sampled data representing an electrical signal indicating electrical activity of a patient heart over multiple heart beat cycles. Signal processor 15 in step 955 employs a heart cycle synchronization signal in automatically decomposing the received sampled data to multiple different subcomponent signals in the time domain. In step 958 processor 15 associates individual decomposed subcomponents with corresponding different cardiac rotors and determined characteristics of the subcomponents indicating relative significance of the rotors in a cardiac atrial condition. The subcomponent characteristics indicate amplitude of individual subcomponents. Signal processor 15 decomposes a portion of the received sampled data in a time interval comprising from start of a P wave to a peak of a succeeding R wave representing a depolarization and repolarization time interval in an individual heart cycle and in multiple successive heart cycles.

In one embodiment, signal processor 15 automatically decomposes the received sampled data to multiple different subcomponent signals in the time domain using empirical mode decomposition. In another embodiment, signal processor 15 automatically decomposes the received sampled data to multiple different subcomponent signals in the time domain using at least one of, independent component analysis and principal component analysis. The received sampled data comprises intra-cardiac data indicating electrical activity of a patient heart from multiple sites in a heart and signal processor 15 automatically associates the multiple different subcomponent signals with anatomical location and provides data indicating relative significance and anatomical location of the rotors in a cardiac atrial condition.

Signal processor 15 automatically determines a number of rotors in response to a rotor having characteristics exceeding a threshold. The rotor characteristics are derived in response to at least one of, (a) an energy value and (b) a frequency. Further, processor 15 automatically determines a number of rotors in response to characteristics of the decomposed subcomponents and rotors having an energy characteristic exceeding a threshold. Processor 15 automatically determines at least one of, (a) a signal frequency ratio associated with component frequencies of a single subcomponent and (b) a signal frequency ratio associated with dominant component frequencies of different subcomponents. Processor 15 provides a subcomponent characteristic value by averaging characteristic values over multiple heart cycles. Processor 15 determines a standard deviation or variance of determined characteristics of the subcomponents and determines a ratio of an average of multiple characteristic values to a standard deviation or variance of multiple characteristic values.

In step 960, a reproduction device (display 13) provides data indicating the subcomponent characteristics indicating relative significance of the rotors in a cardiac atrial condition. In step 963, treatment processor 34 automatically provides data indicating treatment suggestions in response to the data indicating relative significance and anatomical location of the rotors. the treatment suggestions comprise at least one of, (a) prioritized location of anatomical sites for ablation, (b) location of anatomical sites for electrical stimulation and (c) medication. Processor 15 in step 966 stores mapping information in repository 17. The mapping information associates ranges and thresholds of subcomponent characteristic values and values derived from the characteristic values with corresponding medical conditions. The predetermined mapping information associates ranges of characteristic values with particular patient demographic characteristics and with corresponding medical conditions and the system uses patient demographic data including at least one of, age weight, gender and height in comparing a characteristic value with the ranges and generates an alert message indicating a potential medical condition. In step 969 comparator 29 compares at least one of the subcomponent characteristic values or a value derived from a subcomponent characteristic value with a threshold value and range to provide a comparison indicator identifying a medical condition such as Atrial fibrillation. In step 972, patient monitor 31, in response to the comparison indicator indicating a calculated subcomponent characteristic value exceeds a threshold value or lies in a range, generates an alert message associated with the threshold. The process of FIG. 13 terminates step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The processes and applications may, in alternative embodiments, be located on one or more (e.g., distributed) processing devices on a network linking the system units. Any of the functions and steps provided in the Figures may be implemented in hardware, software or a combination of both.

The system and processes of FIGS. 1-12 are not exclusive. Other systems and processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system quantifies atrial electrophysiological signal waveform changes using time domain subcomponent analysis to provide atrial arrhythmia type, abnormal excitation rotor location and atrial pathology severity for improved diagnosis, such as of atrial fibrillation arrhythmia. Further, the processes and applications may, in alternative embodiments, be located on one or more (e.g., distributed) processing devices on a network linking the units of FIG. 1. Any of the functions and steps provided in FIGS. 1-12 may be implemented in hardware, software or a combination of both.

APPENDIX

Figure 12:
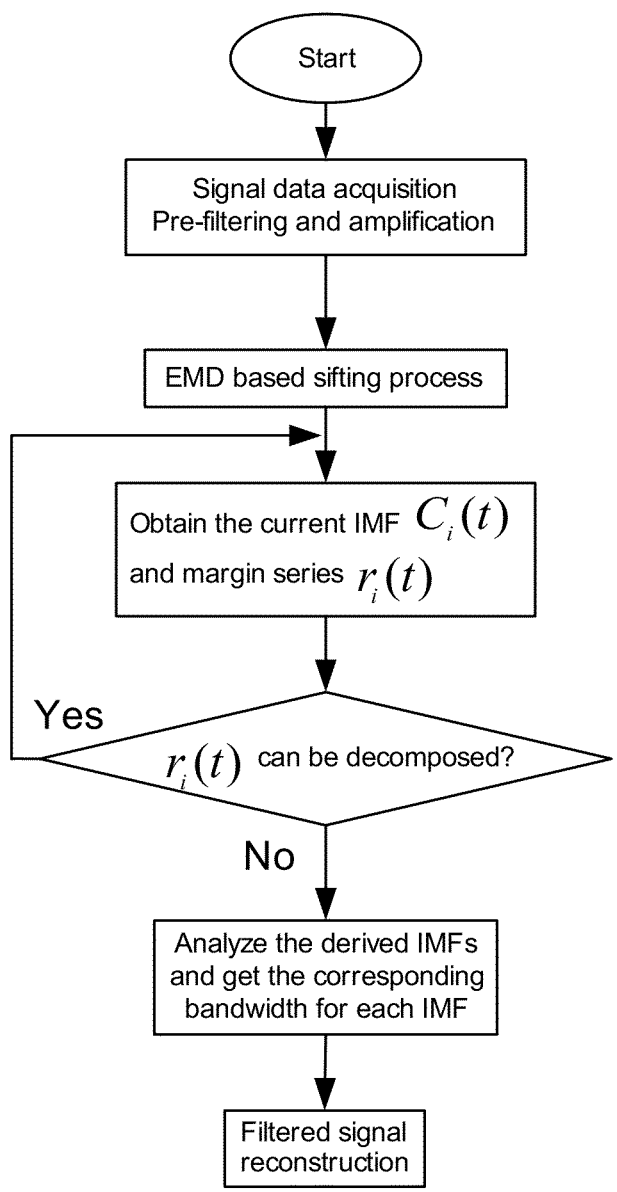
FIG. 12 shows a known empirical mode decomposition (EMD) based signal decomposition method.

FIG. 12 shows a known empirical mode decomposition (EMD) based signal decomposition method. In EMD decomposition if the number of maxima or minima of data series X(t) is larger than the number of up-zero (or down-zero) crossing points by two, then the series needs to be forced to be stationary. The detailed procedures are as follows:
(i) Pick out the maxima of the series X(t) and calculate the upper envelop with a cubic spline function.
(ii) Pick out the minima of the series X(t) and calculate the lower envelop with a cubic spline function.
Then mean envelop $m_1(t)$ of the series X(t) is the mean value of the upper and lower envelops. A new series $h_1$ with low frequency removed is calculated by subtracting the mean envelop from the series X(t):

$$X(t) - m_1(t) = h_1(t)$$

Generally speaking, $h_1$ is still a non-stationary series, so the above procedure is repeated k times until the mean envelop is approximately zero, so the first IMF component $C_1(t)$ is obtained:

$$h_{k-1}(t) - m_{1k}(t) = h_{1k}(t)$$

$$C_1(t) = h_{1k}(t)$$

The first IMF component represents the highest frequency component of the original series. The second IMF component $C_2(t)$ can be obtained from $r_1(t)$ which is calculated by subtracting the first IMF component from series X(t). Such procedure needs to be repeated until the last margin series $r_n(t)$ cannot be decomposed further, here $r_n(t)$ represents the mean value or trend of the original series.

$$r_1(t) - C_2(t) = r_2(t), \ldots, r_n(t) - C_n(t) = r_n(t)$$

The procedure has been termed a "sifting" procedure. Finally, the original series can be presented by a sum of the IMF components and a mean value or trend:

$$X(t) = \sum_{j=1}^{n} C_j(t) + r_n(t)$$

Since an IMF component (IMFi) is a series with a definite characteristic scale, the "sifting" procedure decomposes the original series to a superimposition of waves with various scales. An IMF component can be either linear or nonlinear.

What is claimed is:

1. A system for heart performance characterization and abnormality detection, comprising:
    an interface for receiving sampled data representing an electrical signal indicating electrical activity of a patient heart over a plurality of heart beat cycles;
    a signal processor for automatically for an individual heart cycle
        decomposing a portion of the sampled data within a heart cycle associated with atrial activity, to a plurality of different subcomponent signals in a time domain,
        associating individual decomposed subcomponents of said portion with corresponding different cardiac rotors and determined characteristics of the decomposed subcomponents indicating relative significance of the different cardiac rotors in a cardiac atrial condition; and
    a reproduction device for providing data indicating the determined characteristics of the decomposed subcomponents indicating relative significance of the different cardiac rotors in a cardiac atrial condition.

2. A system according to claim 1, wherein
    said determined characteristics of the decomposed subcomponents indicate amplitude of individual subcomponents and whether individual rotor components are relatively fast or slow and
    said signal processor decomposes a portion of the received sampled data in a time interval from start of a P wave to a peak of a succeeding R wave, representing a depolarization and repolarization time interval in an individual heart cycle.

3. A system according to claim 2, wherein
    said signal processor decomposes said portion of the sampled data in a plurality of successive heart cycles.

4. A system according to claim 1, wherein
    said sampled data comprises intra-cardiac data indicating electrical activity of the patient heart from a plurality of sites in the patient heart and said signal processor automatically associates said plurality of different subcomponent signals with anatomical location and provides data indicating relative significance and anatomical location of the different cardiac rotors in a cardiac atrial condition.

5. A system according to claim 4, including
    a treatment processor for automatically providing data indicating treatment suggestions in response to said data indicating relative significance and anatomical location of the different cardiac rotors.

6. A system according to claim 5, wherein
    said treatment suggestions comprise at least one of, (a) prioritized location of anatomical sites for ablation, (b) location of anatomical sites for electrical stimulation and (c) medication.

7. A system according to claim 1, including
    a comparator for comparing at least one value of said determined characteristics of the decomposed subcomponents or a value derived from a value of said determined characteristics of the decomposed subcomponents with a threshold value to provide a comparison indicator; and
    a patient monitor for in response to said comparison indicator indicating a calculated subcomponent characteristic value exceeds the threshold value, generating an alert message associated with the threshold value.

8. A system according to claim 1, wherein
said signal processor automatically determines a number of rotors in response to the rotors having characteristics exceeding a threshold.

9. A system according to claim 8, wherein
The characteristics of the rotors are derived in response to at least one of, (a) an energy value and (b) a frequency.

10. A system according to claim 1, wherein
said signal processor automatically determines a number of rotors in response to characteristics of said decomposed subcomponents.

11. A system according to claim 1, wherein
said signal processor automatically decomposes the sampled data to a plurality of different subcomponent signals in the time domain using empirical mode decomposition.

12. A system according to claim 1, wherein
said signal processor automatically decomposes the sampled data to a plurality of different subcomponent signals in the time domain using at least one of, (a) independent component analysis and (b) principal component analysis.

13. A system according to claim 1, wherein
said signal processor automatically determines a number of rotors in response to a rotor signal having an energy characteristic exceeding a threshold.

14. A system according to claim 1, wherein
said signal processor automatically determines at least one of, (a) a signal frequency ratio associated with component frequencies of a single subcomponent and (b) a signal frequency ratio associated with dominant component frequencies of different subcomponents.

15. A system according to claim 1, wherein
said signal processor employs a heart cycle synchronization signal in automatically decomposing the sampled data.

16. A system according to claim 1, wherein
said signal processor provides a subcomponent characteristic value by averaging characteristic values over a plurality of heart cycles.

17. A system according to claim 1, wherein
said signal processor determines a standard deviation or variance of the determined characteristics of the decomposed subcomponents.

18. A system according to claim 1, wherein
said signal processor determines a ratio of an average of a plurality of characteristic values to a standard deviation or variance of a plurality of characteristic values.

19. A system according to claim 1, including
a repository of mapping information, associating ranges of characteristic values with corresponding medical conditions and including
a comparator for comparing characteristic values with said ranges to provide a comparison indicator identifying a medical condition.

20. A system according to claim 19, wherein
said mapping information associates ranges of the characteristic values with particular patient demographic characteristics and with corresponding medical conditions and said system uses patient demographic data including at least one of, age, weight, gender and height in comparing the characteristic value with said ranges and generates an alert message indicating a potential medical condition.

21. A system according to claim 18, wherein
said medical condition comprises Atrial fibrillation.

22. A method for heart performance characterization and abnormality detection, comprising the activities of:
receiving sampled data representing an electrical signal indicating electrical activity of a patient heart over a plurality of heart beat cycles;
automatically for an individual heart cycle decomposing a portion of the sampled data within a heart cycle associated with atrial activity, to a plurality of different subcomponent signals in a time domain;
automatically associating individual decomposed subcomponents of said portion with corresponding different cardiac rotors and determined characteristics of the decomposed subcomponents indicating relative significance of the different cardiac rotors in a cardiac atrial condition; and
providing data indicating the determined characteristics of the decomposed subcomponents indicating relative significance of the different cardiac rotors in a cardiac atrial condition.

23. A method according to claim 22, wherein
said subcomponent characteristics indicate amplitude of individual subcomponents and including the activity of
decomposing a portion of the received sampled data in a time interval start of a P wave to a peak of a succeeding R wave representing a depolarization and repolarization time interval in an individual heart cycle.

* * * * *